(12) United States Patent
Miyamoto et al.

(10) Patent No.: US 7,560,238 B2
(45) Date of Patent: Jul. 14, 2009

(54) IMMUNOLOGICAL LATEX TURBIDIMETRY METHOD AND REAGENT THEREFOR

(75) Inventors: Atsushi Miyamoto, Tokyo (JP); Tokio Sawai, Tokyo (JP); Takeshi Matsuya, Tokyo (JP); Tsuneo Okuyama, Kanagawa (JP)

(73) Assignee: Mitsubishi Kagaku Iatron, Inc., Tokyo (JP)

( * ) Notice: Subject to any disclaimer, the term of this patent is extended or adjusted under 35 U.S.C. 154(b) by 358 days.

(21) Appl. No.: 10/048,212

(22) PCT Filed: May 30, 2001

(86) PCT No.: PCT/JP01/04526

§ 371 (c)(1),
(2), (4) Date: Jun. 7, 2002

(87) PCT Pub. No.: WO01/92885

PCT Pub. Date: Dec. 6, 2001

(65) Prior Publication Data

US 2002/0182752 A1    Dec. 5, 2002

(30) Foreign Application Priority Data

May 30, 2000    (JP)    ............................. 2000-159729

(51) Int. Cl.
   *G01N 33/00*    (2006.01)
(52) U.S. Cl. ................. 435/7.1; 435/7.9; 435/7.92; 436/501; 436/506; 436/518; 436/533
(58) Field of Classification Search ................. 435/7.1, 435/7.9, 7.92; 436/501, 509, 518, 533
See application file for complete search history.

(56) References Cited

U.S. PATENT DOCUMENTS 4,096,138 A * 6/1978 Scherr .................... 530/363
4,427,781 A * 1/1984 Masson et al. .............. 436/509

FOREIGN PATENT DOCUMENTS

GB    0061857 A1 * 10/1982
JP    48019719 B4 *  3/1973
JP    58-144748 A      8/1983
JP    61-198062 A      8/1986
JP    63-298062 A     12/1988
JP    07140145 A2 *   6/1995
JP    11-023573    *   1/1999
JP    11-23573 A       1/1999

OTHER PUBLICATIONS

Hunter et al. (Int. Arch. Allergy, 36 354-375, 1969).*
Shinoda et al. (Nippon Ishinkin Gakkai Zasshi, 1991, 32 Suppl.2 Proc. Annu. Meet. Jpn. Soc. Med. Mycol. 34th 1990, pp. 83-93, Abstract Only).*
Shinoda et al. (Nippon Ishinkin Gakkai Zasshi, 1991, 32 Suppl.2 Proc. Annu. Meet. Jpn. Soc. Med. Mycol. 34th 1990, pp. 83-93) Full Document Provided.*
Dosa et al. (Immunology, 1979, 38, pp. 509-517).*
K. R. Falchuk et al, Circulating Antibodies To Bovine Albumin In Ulcerative Colitis And Crohn's Disease Characterization Of The Antibody Response, Gastroenterology, 1976, pp. 5-8, vol. 70—No. 1. (XP008040079).
Y. Hanai et al, IgM-lambda Type Monoclonal Gammopathy Of Undetermined Significance Showing Non-Specific Anti-Streptolysin O Activity By A Latex Immumoaggregation Method, Medline/NLM, Oct. 1999, pp. 331-335, vol. 22—No. 5. (XP002310495).
International Search Report.

* cited by examiner

*Primary Examiner*—Lisa V Cook
(74) *Attorney, Agent, or Firm*—Sughrue Mion, PLLC

(57) ABSTRACT

An immunological latex turbidimetry method for analyzing an antigen or antibody in a sample is disclosed, comprising steps of (1) bringing a sample which may contain the antigen or antibody to be analyzed into contact with a protease-treated albumin, and (2) bringing a mixture obtained in the above step (1) into contact with latex particles carrying an antibody or antigen specifically reacting with the antigen or antibody to be assayed, and analyzing a turbidity caused by a latex agglutination reaction. Also disclosed is an immunological latex turbidimetry reagent comprising (1) a first component containing a protease-treated albumin, and (2) a second component containing latex particles carrying an antibody or antigen specifically reacting with an antigen or antibody to be assayed.

6 Claims, No Drawings

IMMUNOLOGICAL LATEX TURBIDIMETRY METHOD AND REAGENT THEREFOR

TECHNICAL FIELD

The present invention relates to an immunological latex turbidimetry method and an immunological latex turbidimetry reagent, each making use of an antigen-antibody reaction. More particularly, the present invention relates to an immunological latex turbidimetry method and an immunological latex turbidimetry reagent, each being capable of reducing a non-specific agglutination reaction, and preferably applied in an automated analyzer. The term "analyze" as used herein includes a measurement to quantitatively or semi-quantitatively determine an amount of an antigen or antibody to be assayed and a detection to judge a presence or absence of an antigen or antibody to be assayed.

BACKGROUND ART

Immunological assay reagents making use of an antigen-antibody reaction are used as a reagent for quantitatively analyzing a particular component, such as an antigen or antibody to be assayed, in a liquid sample. Of the reagents, an immunological latex turbidimetry method is widely used, because a quantitative determination can be carried out by an automated analyzer and easy procedures. In the immunological latex turbidimetry method, an agglutination of the latex particles is analyzed by a change of an absorbance or a turbidity. The agglutination is caused by an antigen-antibody reaction between the latex particles carrying thereon antigens or antibodies, and antibodies or antigens in a liquid sample.

Recently, a simple, quick and high-sensitivity analysis has been desired in an analyzing field using an automated analyzer as above. Thus, an immunological latex turbidimetry method and a reagent therefor have been required to meet the above need.

Up to now, the immunological latex turbidimetry reagent contains a bovine serum albumin (hereinafter sometimes referred to as BSA) and/or a thermally modified BSA, to enhance a sensitivity, accelerate a dispersion of suspended latex particles, or avoid a non-specific agglutination caused by a non-specific binding of proteins or the like in a sample, to the latex. This is because some patients from which samples are taken have antibodies to BSA, due to a recent change of eating habits. The BSA added to an analyzing reagent can take up an anti-BSA antibody of the patient. For example, in an immunological latex turbidimetry reagent carrying an antigen stemmed from a streptococcus haemolyticus component (streptolysin O; hereinafter sometimes referred to as SLO) for detecting an SLO antibody, a thermally modified BSA is added for absorbing the non-specific reaction. However, there still remain samples showing a non-specific reaction which cannot be absorbed only by an addition of the thermally modified BSA. This has been a problem to be solved.

DISCLOSURE OF INVENTION

Accordingly, an object of the present invention is to provide an immunological latex turbidimetry method capable of avoiding an influence of a non-specific reaction, and an improvement of such an avoidance, while maintaining a high specificity to an antigen or antibody to be assayed, and a reagent therefor. In particular, the object of the present invention is to provide an immunological latex turbidimetry method capable of an easy, rapid, and high-sensitivity analysis when applied to an automated analyzer, and a reagent therefor.

The above problem can be solved by the present invention, i.e., an immunological latex turbidimetry method for analyzing antigen or antibody in a sample, comprising steps of:

(1) bringing a sample which may contain the antigen or antibody to be analyzed into contact with a protease-treated albumin; and (2) bringing a mixture obtained in the above step (1) into contact with latex particles carrying an antibody or antigen specifically reacting with the antigen or antibody to be assayed, and analyzing a turbidity caused by a latex agglutination reaction.

Further, the present invention relates to an immunological latex turbidimetry reagent comprising (1) a first component containing a protease-treated albumin, and (2) a second component containing latex particles carrying an antibody or antigen specifically reacting with an antigen or antibody to be assayed.

BEST MODE FOR CARRYING OUT THE INVENTION

According to the present invention, a protease-treated albumin, preferably a protease-treated serum albumin, more preferably a protease-treated BSA, is used as an agent for reducing a non-specific reaction in an immunological latex turbidimetry analysis, whereby a non-specific reaction of latex particles can be avoided without lowering a reagent specificity.

The term "immunological latex turbidimetry analysis" as used herein means an optical analysis of an agglutination phenomenon accompanied by an immunological reaction caused at latex carriers carrying an antigen (or antibody) when brought into contact with an antibody (or antigen) in a sample, by a change of an absorbance or a turbidity.

A sample which may be analyzed by the immunological latex turbidimetry method of the present invention or the immunological latex turbidimetry reagent of the present invention is not particularly limited, so long as it is a sample which may possibly contain an antigen or antibody to be analyzed. For example, the sample may be a liquid taken from a living body and generally used in a clinical examination, such as a serum, plasma, or urine.

The protease-treated albumin used in the present invention is not particularly limited, so long as it is a fragmentated albumin, preferably a fragmentated serum albumin, more preferably a fragmentated BSA, prepared by a protease treatment. The albumin to be treated may be an albumin prepared from a naturally occurring source, a recombinant albumin (preferably a recombinant bovine albumin), or a partially synthesized albumin. The present invention will be explained hereinafter with respect to the BSA, which is a preferred embodiment.

The protease is not particularly limited, so long as it can reduce the non-specific agglutination reaction without lowering a sensitivity of the immunological latex turbidimetry reagent of the present invention, for example, pepsin, papain, or trypsin. The above protease may be used singly or in combination thereof. Of the proteases as above, pepsin is preferable with respect to cost and stability. For example, the protease-treated BSA may be prepared by maintaining the BSA in an acidic condition, and adding a protease thereto. The resulting protease-treated reaction product can be used in the present invention, without purification.

The term "protease treatment" as used herein means a treatment for decomposing a naturally occurring albumin to obtain plural fragments, more particularly, a treatment for decomposing an albumin into about 2 to 10 fragments, preferably 4 to 8 fragments. For example, it is known that a serum albumin can be decomposed by pepsin into 2 to 7 fragments, and the resulting fragment has a molecular weight of about 5000 to 50000. In the present invention, the resulting fragments can be used without separating each of the fragments, that is, in the form of a mixture of the fragments. Alternatively, it is possible to separate the resulting fragments into single fragments, combine a plurality of the separated fragments, for example, 2 to 9 fragments, and use the combined fragments.

A conventional immunological latex turbidimetry method can be applied to the immunological latex turbidimetry method of the present invention, except that, before bringing a sample into contact with latex particles carrying an antibody or antigen, i.e., a latex-particles-suspension, the sample is brought into contact with the protease-treated BSA.

A concentration of the protease-treated BSA to be brought into contact with the sample is not particularly limited, so long as it can inhibit the non-specific reaction and does not influence the latex turbidimetric reaction, but is preferably 0.1 to 1.5%, more preferably 0.35 to 0.8%. The unit "%" as used herein with respect to the concentration of the protease-treated BSA means a mass/volume %, i.e., w/v %. If the concentration is less than 0.1%, the non-specific reaction cannot be sufficiently inhibited. No particular problem arises when the concentration is more than 1.5%. Nevertheless, an advantageous effect cannot be expected with an increase of the concentration. Further, a very high concentration is supposed to influence the latex turbidimetric reaction per se. Therefore, an increase of the concentration over the above upper limit is meaningless in obtaining the advantageous effect of the present invention, that is, in inhibiting the non-specific reaction.

As the latex particles carrying an antigen or antibody, any particles carrying an antigen or antibody which may be used for the known immunological latex turbidimetry reagent may also be used in the present invention.

As the latex particles, conventional latex particles may be used in the present invention. For example, the latex particles may be particles of organic high-molecular weight materials, such as latex particles of polystyrene, styrene-methacrylic acid copolymer, styrene-glycidyl (meth)acrylate copolymer, or styrene-styrene sulfate copolymer. An average particle size of the latex particles may be the same as that of the conventional latex particles, and is not particularly limited.

The antigen or antibody carried on the latex particles is not particularly limited, so long as it can cause the antigen-antibody reaction with the antibody or antigen to be analyzed. For example, an anti-$\beta$2-microglobulin ($\beta$2-M) antibody, anti-fibrin decomposed products D fraction (FDP-D) antibody, anti-fibrin decomposed products E fraction (FDP-E) antibody, anti-fibrin decomposed products DD fraction (FDP-DD) antibody, anti-albumin antibody, anti-ferritin antibody, anti-$\alpha$-fetoprotein (AFP) antibody, insulin, anti-insulin antibody, or an antigen or antibody of Treponema Pallidum (TP), streptolysin O (SLO), or Hepatitis B virus (HBV) may be used.

The latex particles can be sensitized with an antigen or antibody in accordance with a known method, for example, a physically adsorbing method. It is preferable to use the latex particles carrying about a 0.001 to 1 mass % of antigen or antibody.

The non-specific reaction is frequently caused not only by the reaction with the BSA, but also by digested products of the BSA. Hitherto, however, there was no method for coping with the digested products of the BSA. Further, an effect for the digested products of the BSA cannot be expected by an addition of BSA, or the effect is insufficient. Therefore, a technical meaning is particularly significant in that the sample is brought into contact not only with the BSA, but also with the protease-treated BSA before carrying out the antigen-antibody reaction, whereby a part of materials reactive with the BSA and the digested products of the BSA in the sample is masked, and the non-specific reaction caused by the BSA and the digested products of the BSA is inhibited.

Accordingly, the protease-treated albumin can be used instead of or in addition to an albumin, preferably a serum albumin, more preferably a BSA, and/or a modified albumin, preferably a modified serum albumin, more preferably a modified BSA which has been hitherto used for inhibiting the non-specific reaction, in the present invention.

A buffer which may be used in the present invention is not particularly limited, so long as it may be used in a known immunological latex turbidimetry reagent. Examples of the buffer are a tris buffer, a phosphate buffer, a glycine buffer, a borate buffer, a Good's buffer, or the like.

In the present invention, any additives, such as a stabilizer, which may be used in a known immunological latex turbidimetry reagent, may be used, so long as they do not cause a loss of the effect of the present invention. The stabilizer may be, for example, an inorganic salt, such as sodium chloride or sodium azide, a protein such as a bovine serum albumin, or choline chloride. An amount of the stabilizers added is not particularly limited. For example, when sodium chloride is added, the concentration thereof is preferably 50 to 300 mmol/L. The concentration of sodium azide is preferably 0.01 to 1%, the concentration of bovine serum albumin is preferably 0.1 to 10%, and the concentration of choline chloride is preferably 0.1 to 30%.

The immunological latex turbidimetry reagent of the present invention contains the protease-treated BSA and the latex particles carrying thereon an antigen or antibody, and is a system composed of at least two reagent-components. Because the protease-treated BSA must be brought into contact with the sample before the sample is brought into contact with the latex particles in the present invention, the protease-treated BSA is contained at least in a reagent-component which is brought into contact with the sample before the antigen-antibody reaction is carried out. After the reagent-component containing the protease-treated BSA is brought into contact with the sample, the sample is brought into contact with a reagent-component containing the latex particles, to carry out the antigen-antibody reaction. The reagent-component containing the latex particles may or may not contain the protease-treated BSA.

In general, a conventional known immunological latex turbidimetry reagent is composed of a suspension of the latex particles carrying an antigen or antibody and a buffer stabilizing the sample, whereas the immunological latex turbidimetry reagent of the present invention further contains the protease-treated BSA in addition thereto. Therefore, the immunological latex turbidimetry reagent of the present invention may be composed of the same ingredients as those of the known immunological latex turbidimetry reagent generally used, except that the protease-treated BSA is contained at least in a reagent-component. As mentioned above, latex particles, an antigen or antibody, a buffer, and/or additives which may be used in the conventional known immunological latex turbidimetry reagent may also be used in the immunological latex turbidimetry reagent of the present invention, as they are. Further, an albumin, preferably serum albumin, more preferably BSA, and/or a modified albumin, preferably a modified serum albumin, more preferably a modified BSA which has been used to inhibit the non-specific reaction may also be used in the present invention.

When the immunological latex turbidimetry reagent of the present invention is composed of the two reagent-components system, it may be, for example, composed of a first reagent, i.e., a first component, containing a buffer for stabilizing a sample and a protease-treated BSA, and a second reagent, i.e., a second component, containing latex particles carrying thereon an antigen or antibody.

The immunological latex turbidimetry reagent of the present invention may be a system of three reagent-components, but is preferably a system of two reagent-components, because the number of the reagent-components is small and the procedures for the analysis can be simplified.

A concentration of the protease-treated BSA in the immunological latex turbidimetry reagent of the present invention is not particularly limited, so long as the non-specific reaction can be inhibited when the protease-treated BSA contained in the reagent of the present invention is brought into contact with the sample, and the latex turbidimetric reaction per se is not influenced. For example, when the reagent of the present invention is the two reagent-component system composed of the first reagent containing the buffer for stabilizing the sample and the protease-treated BSA, and the second reagent containing the latex particles carrying an antigen or antibody, an amount of the protease-treated BSA in the first reagent may be preferably 0.1 to 1.5%, more preferably 0.35 to 0.8%. When the amount is less than 0.1%, the non-specific reaction cannot always be sufficiently inhibited. No particular problem arises when the amount is more than 1.5%. Nevertheless, an advantageous effect cannot be expected with an increase of the concentration. Further, a very high concentration is supposed to influence the latex turbidimetric reaction per se. Therefore, an increase of the concentration over the above upper limit is meaningless in obtaining the advantageous effect of the present invention, that is, in inhibiting the non-specific reaction.

A method for adding the protease-treated BSA is not limited. For example, when the reagent of the present invention is the two reagent-component system composed of the first reagent-component containing the buffer for stabilizing the sample and the protease-treated BSA, and the second reagent-component containing the latex particles carrying an antigen or antibody, a predetermined amount of the protease-treated BSA may be dissolved in the buffer for stabilizing a sample.

An embodiment of the immunological latex turbidimetry reagent of the present invention is not particularly limited. However, the immunological latex turbidimetry reagent of the present invention is suitable for an analysis using an automated analyzer, and thus is preferably used as an immunological latex turbidimetry reagent for an automated analysis. It is particularly preferable for an immunological latex turbidimetry analysis of a streptolysin O (SLO) antibody.

More particularly, a preferable embodiment of the immunological latex turbidimetry reagent of the present invention is as follows:

(A) an immunological latex turbidimetry reagent for an automated analysis, comprising a first reagent-component containing the protease-treated BSA (preferably at an amount of 0.1 to 1.5%) in the buffer for stabilizing a sample, and a second reagent-component, that is, a suspension of the latex particles carrying thereon an antigen or antibody; or (B) an immunological latex turbidimetry reagent for an automated analysis for detecting an SLO antibody, comprising a first reagent-component containing the protease-treated BSA (preferably at an amount of 0.1 to 1.5%) in the buffer for stabilizing a sample, and a second reagent-component, that is, a suspension of the latex particles carrying thereon an SLO antigen.

As a concrete embodiment of the immunological latex turbidimetry reagent of the present invention, a two reagent-components system composed of a first reagent-component containing the buffer for stabilizing a sample and protease-treated BSA, and a second reagent-component containing the latex particles carrying thereon an antigen or antibody is shown as follows (concentrations given below are preferable ranges thereof in the reagent, but do not limit the scope of the present invention):

A first reagent-component, a solution containing the following components (1) to (3),
(1) 0.1 to 1.5% protease-treated BSA,
(2) 20 to 1000 mmol/L buffer, pH 4 to 12, and
(3) 50 to 300 mmol/L sodium chloride.

A second reagent-component, a suspension containing the following components (4) to (6),
(4) 20 to 1000 mmol/L buffer, pH 4 to 12,
(5) 0.01 to 0.5w/v% latex particles carrying thereon an antigen or antibody, and
(6) 50 to 300 mmol/L sodium chloride.

The buffer used in the first and second reagent-components may be, for example, a tris buffer, a phosphate buffer, a glycine buffer, a borate buffer, or a Good's buffer. The first reagent-component can be prepared, for example, by mixing 0.1 to 1.5% protease-treated BSA to a buffer.

EXAMPLES

The present invention now will be further illustrated by, but is by no means limited to, the following Examples.

Example 1

Preparation of a Protease-Treated BSA

A bovine serum albumin (Sigma; 500 mg) was added to 10 mL of purified water. The whole was allowed to stand at room temperature for 1 hour, and a pH value was adjusted to 3.0 by adding formic acid with stirring by a spinning bar. The product was allowed to stand at room temperature for 30 minutes, then, 167 µL of a pepsin solution (0.01 mol/L hydrochloric acid solution containing pepsin at a concentration of 1 mg/mL) was added thereto with stirring by a spinning bar. The whole was allowed to stand in a thermostatic chamber at 25° C. for 30 minutes. Then, a pH value was adjusted to 7.0 by 2 mol/L tris solution with stirring by a spinning bar, and sodium azide was added so that its concentration became 0.1%, to obtain a protease-treated BSA.

Example 2

Measurement of a Streptolysin O (SLO) Antigen in Serum (1) Preparation of a Second Reagent (A Liquid Suspension of Latex Carrying a Streptolysin O Antigen)

Carbodiimide (40 mg) was added to 38 mL of a liquid suspension of polystyrene particles (latex concentration=5%, average particle size=0.18 pm), and then, 20 mL of a solution containing 2.8 mg/mL streptolysin O antigen diluted with 10 mmol/L borate buffer (pH 8.2). The whole was mixed, and shaken at 4° C. overnight. Then, 9.5 mL of 20% lysine solution was added. The whole was allowed at stand for 0.5 hour, and centrifuged to obtain a residue, that is, latexes carrying the streptolysin O antigen. To the resulting residue, 190 mL of an aqueous solution containing 0.5% bovine serum albumin was added, and the whole was allowed to stand for 0.5 hour. Then, a residue (i.e., latexes carrying the streptolysin O antigen) prepared by centrifugation was suspended by adding 950 mL of 10 mmol/L borate buffer (pH 8.2), to obtain a second reagent-component for the immunological latex turbidimetric analysis reagent of the present invention.

(2) Preparation of a First Reagent (Buffer)

As a first reagent-component for the immunological latex turbidimetric analysis reagent of the present invention, 0.17 mol/L tris buffer (pH 8.2) containing 0.31 mol/L sodium chloride, 4.5 mmol/L EDTA, 0.2% bovine serum albumin, 0.1% gelatin, and 0.8% protease-treated BSA prepared in Example 1 [final concentration in a system containing equal amounts of the first reagent-component and the second reagent-component=0.4%] was prepared.

For comparison, a comparative buffer (a comparative first reagent) composed of the same ingredients as those in the first reagent for the immunological latex turbidimetric analysis reagent of the present invention, except that the protease-treated BSA was not contained, was prepared.

(3) Preparation of a Liquid Sample

Four sera samples were used as a non-specific sample. An anti-SLO antibody value of more than a measurable upper limit (600 IU/mL) was obtained in the four sera samples by the conventional immunological latex turbidimetry method, whereas the four sera samples were judged as normal by a Rantz-Randall method. It was considered that the non-specific samples showed the high values of the anti-SLO antibody due to the non-specific agglutination. As a control sample, a human normal serum was used.

(4) Measurement by an Automated Analyzer

To 135 μL of the first reagent of the present invention prepared in Example 2(2), 2 μL of the liquid sample prepared in Example 2(3) was added and stirred in a glass cell. The whole was allowed to stand at 37° C. for about 5 minutes. Then, 135 μL of the second reagent prepared in Example 2(1) was added with stirring, and an amount of change in an optical density at a wave length of 700 nm in a range from a point after 30 seconds to a point after 190 seconds. An automated analyzer (Hitachi 7170S, Hitachi Ltd.) was used in the above procedures.

For Comparative Example, the above procedures were repeated except that the comparative buffer (the comparative first reagent) prepared in Example 2(2) was used instead of the first reagent-component.

The results are shown in Table 1. The analyzer was not able to measure a change of absorbance (DABS) in Comparative Example, whereas the SLO was accurately measured according to the present invention using the present reagent.

TABLE 1

|  | Example (IU/mL) | Comparative Example (IU/mL) |  |
|---|---|---|---|
| Normal serum | 24.2 | 26.2 |  |
| Non-specific sample 1 | 47.8 | 4774 | (over absorbance) |
| Non-specific sample 2 | 39.1 | 11136 | (over absorbance) |
| Non-specific sample 3 | 30.3 | 5300 | (over absorbance) |
| Non-specific sample 4 | 47.8 | 8391 | (over absorbance) |

INDUSTRIAL APPLICABILITY

The immunological latex turbidimetry reagent of the present invention exhibits a high sensitivity as a reagent, and has an advantageous effect of reducing the non-specific reaction. Therefore, according to the present invention, an error measurement due to the non-specific reaction can be decreased, and a high-sensitivity analysis using an automated analyzer can be easily and rapidly carried out.

As above, the present invention is explained with reference to particular embodiments, but modifications and improvements obvious to those skilled in the art are included in the scope of the present invention.

The invention claimed is:

1. An immunological latex turbidimetry method for analyzing an antigen or antibody in a sample, comprising steps of:
   (1) bringing a sample which may contain the antigen or antibody to be analyzed into contact with a protease-treated fragmented bovine serum albumin; and
   (2) bringing a mixture obtained in the above step (1) into contact with latex particles carrying bovine serum albumin and an antibody or antigen that specifically binds to the antigen or antibody to be assayed, and analyzing a turbidity caused by a latex agglutination reaction.

2. The immunological latex turbidimetry method according to claim 1 wherein the protease is a pepsin.

3. The immunological latex turbidimetry method according to claim 1 wherein the antibody to be analyzed is an anti-streptolysin O antibody, and the antigen carried on the latex particles is a streptolysin O antigen.

4. An immunological latex turbidimetry reagent comprising (1) a first component containing a protease-treated fragmented bovine serum albumin, and (2) a second component containing latex particles carrying bovine serum albumin and an antibody or antigen that specifically binds to an antigen or antibody to be assayed.

5. The immunological latex turbidimetry reagent according to claim 4 wherein the protease is a pepsin.

6. The immunological latex turbidimetry reagent according to claim 4 wherein the antibody to be analyzed is an anti-streptolysin O antibody, and the antigen carried on the latex particles is a streptolysin O antigen.

* * * * *